(12) United States Patent
He et al.

(10) Patent No.: US 7,601,835 B2
(45) Date of Patent: Oct. 13, 2009

(54) PREPARATION OF FAMCICLOVIR AND OTHER PURINE DERIVATIVES

(75) Inventors: Liang He, Chongqing (CN); Weiping Jiang, Chongqing (CN)

(73) Assignee: Arrow International Limited, Valletta (MT)

( * ) Notice: Subject to any disclaimer, the term of this patent is extended or adjusted under 35 U.S.C. 154(b) by 378 days.

(21) Appl. No.: 11/270,777

(22) Filed: Nov. 10, 2005

(65) Prior Publication Data

US 2006/0264629 A1 Nov. 23, 2006

(30) Foreign Application Priority Data

May 20, 2005 (GB) .................... 0510345

(51) Int. Cl.
*C07D 473/32* (2006.01)
*C07D 473/28* (2006.01)
*C07D 473/02* (2006.01)

(52) U.S. Cl. .................. 544/277; 544/264; 544/265

(58) Field of Classification Search ........... 544/264, 544/265, 277
See application file for complete search history.

(56) References Cited

U.S. PATENT DOCUMENTS

| 5,036,071 A | 7/1991 | Johansson et al. |
| 5,138,057 A | 8/1992 | Geen et al. |
| 5,684,153 A | 11/1997 | Geen et al. |
| 5,917,041 A | 6/1999 | Daluge et al. |
| 6,761,767 B2 | 7/2004 | Hijiya et al. |
| 2005/0215787 A1* | 9/2005 | Joshi et al. .................. 544/276 |

FOREIGN PATENT DOCUMENTS

| EP | 0 141 927 A2 | 5/1985 |
| EP | 0 141 927 A3 | 5/1985 |
| EP | 0 182 024 A2 | 5/1986 |
| EP | 0 182 024 A3 | 5/1986 |
| EP | 0 352 953 A2 | 1/1990 |
| EP | 0 352 953 A3 | 1/1990 |
| WO | WO 95/21161 A1 | 8/1995 |
| WO | WO 95/28402 A2 | 10/1995 |
| WO | WO006573 A1 * | 2/2000 |
| WO | WO 2004/110343 A2 | 12/2004 |
| WO | WO 2004/110343 A3 | 12/2004 |

OTHER PUBLICATIONS

Kalayanov, et al, Synthesis (2004), (12), 2026-2034.*
Choudary et al., Nucleosides & Nucleotides (1996), 15(5), 981-994.*
Brand, B., et al., "Convenient Syntheses of 9-[4-Hydroxy-3-(acetoxymethyl)butyl]-2-amino-9*H*-purine (Famciclovir)," *Tetrahedron* 55:5239-5252, Elsevier Science Ltd. (1999).
Ciapetti, P., and Taddei, M., "A Simple Preparation of N-Vinyl Derivatives of DNA Nucleobases,"0 *Tetrahedron* 54:11305-11310, Elsevier Science Ltd. (1998).
Geen, G.R., et al., "Regioselective alkylation of guanines using 2-acetoxytetrahydrofurans," *Tetrahedron Lett.* 42:1781-1784, Elsevier Science Ltd. (2001).
Harnden, M.R., et al., "Prodrugs of the Selective Antiherpesvirus Agent 9-[4-Hydroxy-3-(hydroxymethyl)but-1-yl]guanine (BRL 39123) with Improved Gastrointestinal Absorption Properties," *J. Med. Chem.* 32:1738-1743, American Chemical Society (1989).
Harnden, M.R., et al., "Crystal and Molecular Structures of the Antiviral Acyclonucleoside 9-[4-Hydroxy-3-(Hydroxymethyl)Butyl]Guanine (BRL39123, Penciclovir) and Its Prodrug 9-[4-Acetoxy-3-(Acetoxymethyl)Butyl]-2-Aminopurine (BRL 42810, Famciclovir)," *Nucleoside & Nucleotides* 9:499-513, Marcel Dekker, Inc.
Izawa, K. and Shiragami, H., "Practical syntheses of antiviral nucleosides," *Pure & Appl. Chem.* 70:313-318, International Union of Pure and Applied Chemistry (1998).

* cited by examiner

*Primary Examiner*—Mark L Berch
(74) *Attorney, Agent, or Firm*—Sterne, Kessler, Goldstein & Fox P.L.L.C.

(57) ABSTRACT

Purine derivatives of formula I, substituted at the 9-position, are prepared from a chloro substituted purine starting material, first making an alkyl substitution at the 9-position, then forming the desired esterified side chain, reducing this and hydrogenating the resultant diol prior to addition of alkyl carbonyl groups.

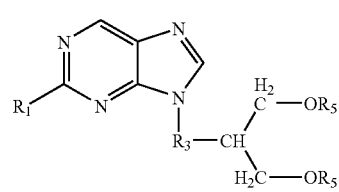

(I)

11 Claims, No Drawings

PREPARATION OF FAMCICLOVIR AND OTHER PURINE DERIVATIVES

FIELD OF INVENTION

The present invention relates to the preparation of various 9-substituted purine derivatives, including famciclovir.

BACKGROUND OF THE INVENTION

Famciclovir (9-[4-acetoxy-3-(acetoxymethyl)but-1-yl]-2-aminopurin) is one of a number of compounds known to have useful antiviral activity and described, for example, in EP 141,927. Famciclovir has antiviral activity relevant for treatment of a number of viral infections, including herpes simplex, varicella-zoster and hepatitis.

A number of different routes for preparation of purine derivatives such as famciclovir are known, including those described in EP 182,024, EP 141,927, EP 352,953, U.S. Pat. No. 5,684,153, U.S. Pat. No. 5,138,057, U.S. Pat. No. 5,917,041, U.S. Pat. No. 6,761,767, Geen et al. (2001) in Tet. Lett. 42(9) 1781, Harnden et al. (1989) in J. Med. Chem. 32(8) 1738, Harnden et al. (1990) in Nucleosides and Nucleotides 9(4) 499, Izawa and Shiragami (1998) in Pure and Applied Chemistry 70(2) 313 and WO 2004/110343.

One method, set out below in Scheme 1, is known from EP 182,024 and U.S. Pat. Nos. 5,684,153; 5,138,057 and 6,761,767. Here the X on starting compound 6 is either halogen or any other leaving group such as tosyl or mesyl.

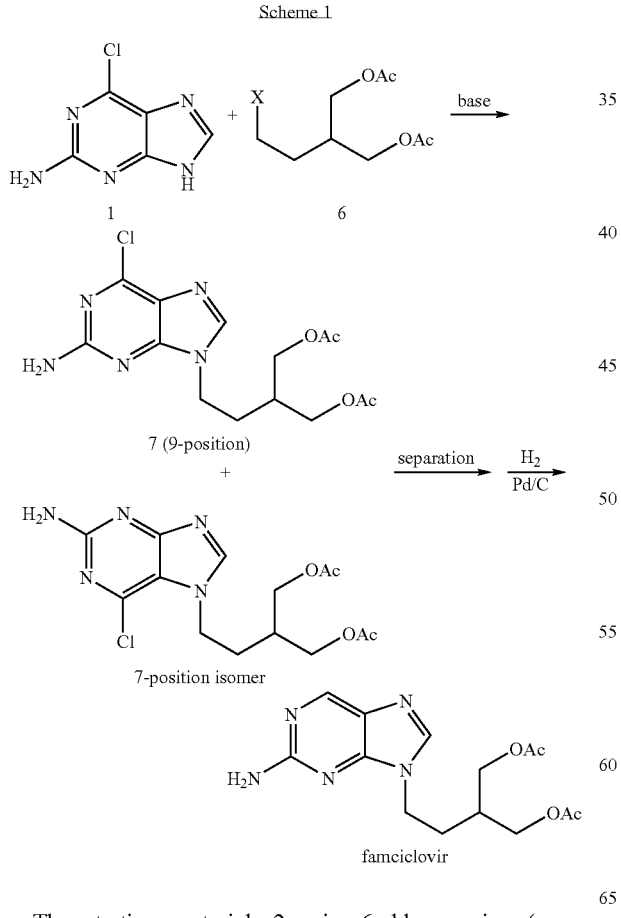

The starting material, 2-amino-6-chloro-purine (compound 1), is commercially available at a reasonable price. However, a common problem associated with this process is lack of regioselectivity as the undesired 7-position isomer is generated simultaneously, reducing yield and requiring a separation step to remove this unwanted (inactive) isomer.

A further method, set out as Scheme 2, is known from U.S. Pat. No. 5,971,041.

The method of Scheme 2 tries to address this problem in order to maximize the percentage of desired 9-substituted compound by carefully controlling the reaction conditions. However, starting compounds 8 and 9 are not commercially available and have to be prepared separately. Also, the overall yield for famciclovir is low, less than 30%.

A more recent method, set out as Scheme 3, is described in WO 2004/110343.

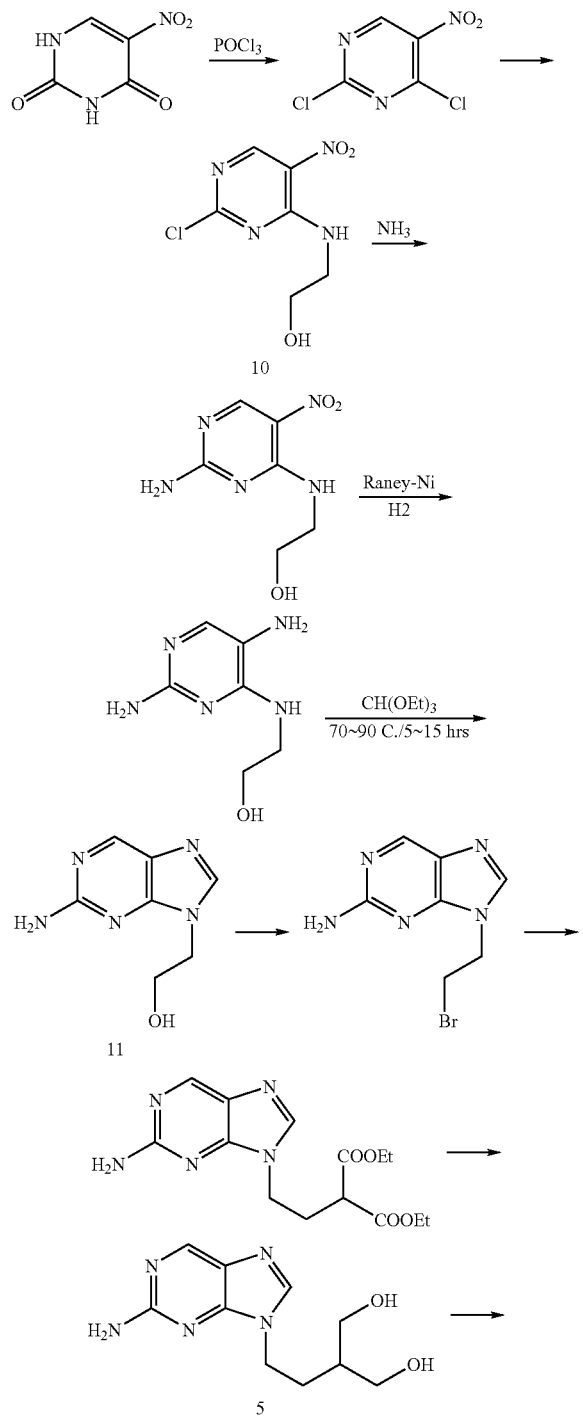

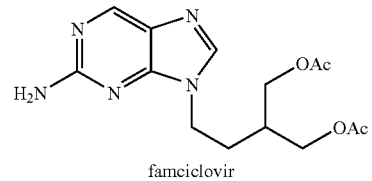

famciclovir

But this process only produce famciclovir at about 18% overall yield. Again, compound 11 used in this process is not commercially available and has to be prepared from nitrouracil.

The methods described in scheme 2 and 3 provide a solution to the above mentioned regioselectivity problem by introducing the alkyl side-chain first onto the desired 9-position before the formation of fused imidazole ring. Nevertheless, a common drawback in these methods is their lengthy procedure and overall low yield.

An object of the present invention is to provide an alternative process for preparation of purine derivatives such as famciclovir.

An object of specific embodiments of the invention is to provide a process for preparation of these purine derivatives with improved efficiency, for example with a reduced number of steps and/or improved yield of the desired end product.

SUMMARY OF THE INVENTION

According to the present invention, there is provided a method for preparation of a purine derivative of formula I

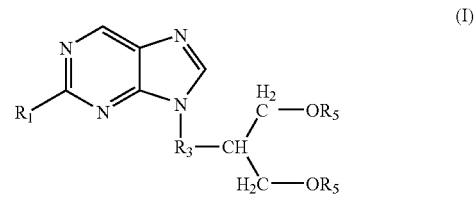

comprising reacting a compound of formula VI

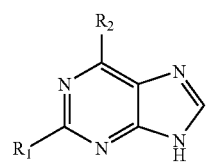

with X—$R_3$—X to form a compound of formula V

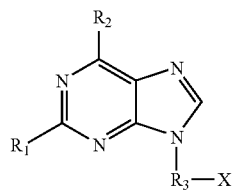

wherein $R_1$ is selected from the group consisting of amino, hydroxyl and $C_{1-6}$ alkyl (optionally substituted), $R_2$ is halo or an electron withdrawing group, $R_3$ is $C_{1-6}$ alkyl (optionally substituted) and each X is independently a leaving group. All substituents are optionally protected.

It has been found that employment of this step results in formation of the 9-substituted compound of formula V with high regioselectivity, the 9-substituted isomer being obtainable in specific embodiments of the invention at a ratio of 15-20:1 compared with the formation of the contaminating 7-substituted isomer. Hence, there is significantly reduced contamination by the unwanted isomer, reduced need for separation of the products of this reaction step and improved yield overall of the desired end product.

In a further method of the invention, a desired purine derivative of formula I is obtained in a method comprising hydrogenating an intermediate diol of formula III

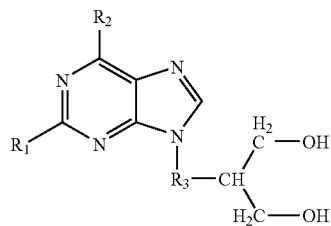

so as to yield a compound of formula II.

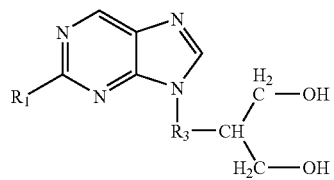

In operation of a method of the invention employing this step, there is high yield of the desired intermediate II and absence of a trans-acetylation side-reaction seen in prior art methods in which the corresponding hydrogenation step is carried out on a diester intermediate.

A preferred method of the invention employs both the steps detailed above, namely reacting a compound of formula VI with X—$R_3$—X to form a compound of formula V and also hydrogenating an intermediate compound of formula III so as to form a compound of formula II.

DETAILED DESCRIPTION OF THE PREFERRED EMBODIMENTS

A preferred embodiment of the invention provides a five step process for manufacture of a compound of formula I from a starting material of formula VI. Initial formation of compound V and an intermediate hydrogenation step are as described above. Other steps are as follows.

A compound of formula V can be converted to a compound of formula IV

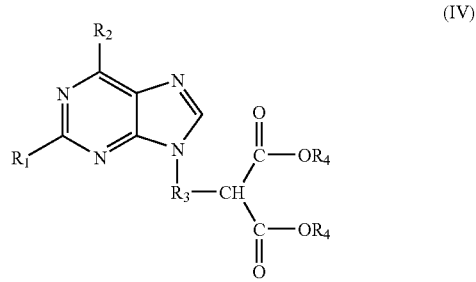

by reaction of compound V with $CH_2(COOR_4)_2$ typically under basic conditions, wherein each $R_4$ is independently a group such that subsequent hydrogenation yields a diol. $R_4$ can be $C_{1-6}$ alkyl (optionally substituted by halo, amino, hydroxyl 1 and/or $C_{1-6}$ alkyl), preferably $C_{1-3}$ alkyl. Generally, both $R_4$ groups are the same.

The compound of formula IV can be then subjected to a reduction reaction using a reducing agent to yield a diol compound of formula III.

The compound of formula II can be converted into the end product of formula I by reaction with $(R_5)_2O$, wherein each $R_5$ is independently selected from $C_{1-6}$ alkyl carbonyl, preferably $C_{1-3}$ alkylcarbonyl. Generally, both $R_5$ groups are the same.

For preparation of famciclovir, in accordance with a preferred embodiment of the invention, $R_1$ is amino, $R_2$ is chloro, $R_3$ is ethyl and $R_5$ is acetyl.

While a process of a specific embodiment has advantageously been used for preparation of the particular compound famciclovir, the process more generally may be employed to obtain other purine derivatives with different side chains located at the 9-position of the purine. For instance, the $R_5$ group, acetyl of famciclovir, can be replaced by any alkylcarbonyl group, especially $C_{1-6}$ alkyl carbonyl, preferably $C_{1-3}$ alkyl carbonyl, optionally substituted by, for example, halo, hydroxyl and/or $C_{1-6}$ alkyl. Separately, the 2-substituted butyl of famciclovir ($R_3CH$) can be replaced by another alkyl chain (see further discussion below) such as $C_{1-6}$ alkyl, preferably $C_{1-4}$ alkyl, optionally substituted by, for example, halo, amino, hydroxyl and/or $C_{1-6}$ alkyl. Halo or halogen refers throughout to fluoro, chloro, bromo and iodo, preferably bromo or chloro, more preferably chloro.

The 2-amino substituent of famciclovir ($R_1$) can also, and independently from the variations noted elsewhere, be replaced in other embodiments of the invention by an alternative substituent. One option is for there to be no substituent, i.e. a hydrogen. Another option is for the 2-position to be substituted by a group selected from amino, hydroxyl (both optionally protected) or $C_{1-6}$ alkyl, preferably $C_{1-3}$ alkyl, optionally substituted by, for example, amino, hydroxyl and/or $C_{1-6}$ alkyl.

The starting material of a specific embodiment is 2-amino-6-chloro-purine, but can generally be a purine substituted at the 2- and 6-positions in accordance with the above.

Substitution of the purine or purine derivative starting material at the 9-position by an alkyl group, as shown for example in step 1 in the example, can be carried out using X—$C_{2-6}$ alkyl-X, where each X is independently a leaving group such as halogen, p-tosyl, mesyl, triflate, alkylcarbonate, preferably halogen. Solvents suitable for this step include polar solvents such as DMF, DMSO, acetonitrile and mixtures of such. The step is suitably carried out in the presence of base, which can be an inorganic base such as $K_2CO_3$ or $Na_2CO_3$, KOH and/or NaOH or appropriate mixtures of these.

Converting compound V to compound IV (step 2 in the example) is suitably carried out in the presence of a base, which can be $K_2CO_3$ or KOH or even a lithium amide like LDA. The solvent used can be similar to that for step 1. There is not much side reaction at all in this step and yields of about 96% can be obtained.

Converting compound IV to compound III (step 3 in the example) is a reduction of the ester functionality for which a number of known reducing agents are suitable.

The diol on compound III may be hydrogenated to compound II (step 4 in the example) by any suitable catalyst, such as Pt, Pd, raney Ni. Because hydrogenation was carried out in alcoholic solvent in the prior art processes, cross acetylation of solvent occurred, which meant that an acetyl group on the 9-side chain group could be lost to give a 9-substituted purine alcohol. This side reaction is substantially avoided in the present process.

Compound II can be converted to compound I (step 5 in the example) in an inert, organic solvent such as $CH_2Cl_2$, $CH_3Cl$, EtOAc etc, and mixtures thereof. In the example this step is carried out in the presence of the triethylamine though pyridine or any tertiary amines may also be used.

The process described herein addresses the problems discussed in the background art. The starting materials and reactants used in the process are all ready available at a reasonable price. In the specific embodiment, by using compounds VI and 1,2-dibromoethane, the invention forms the desired 9-position alkylated purine in a ratio of 15~20:1 (9-position against 7-position isomer), an improvement over the known methods. The process comprises 5 steps and, as per the example, produced famciclovir with an overall yield of over 40%, again an improvement. Another feature in the process is the operational advantage achieved by hydrogenating a diol instead of a diester, avoiding the trans-acetylation side reactions. Referring to the example, this in turn reduced the potential impurity and increased the yield of the process.

The invention is now described in more detail with reference to a specific embodiment as set out in the following example.

Example 1

Preparation of Famciclovir

Famciclovir was prepared according to the following synthetic scheme:

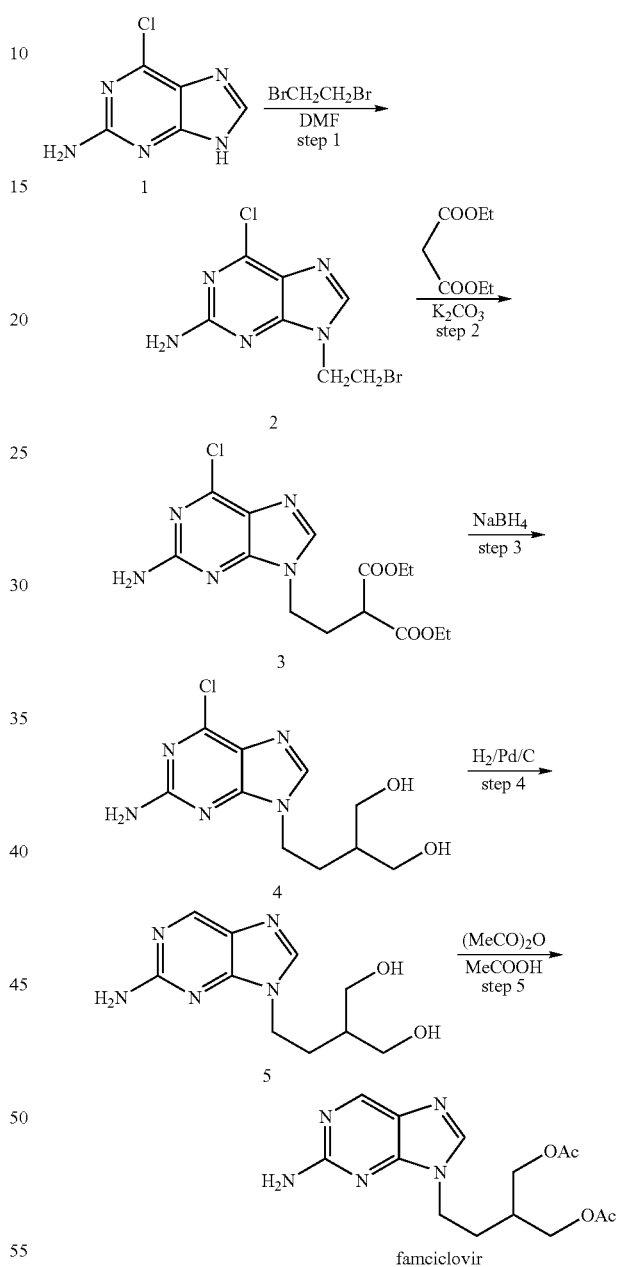

The steps were as follows.

Step 1: Preparation of 2-amino-6-9-chloro-(2-bromoethyl)purine (2)

A mixture of 2-amino-6-chloropurine (33.9 g, 0.2 mol), potassium carbonate (69 g, 0.5 mol) and DMF (340 ml) were placed in a 1 L 3-neck flask, and heated at 60-65° C. for 1 hour. Then the 1,2-dibromoethane (112.8 g, 0.6 mol) was added and the resulting mixture was refluxed for 24 hours.

The reaction mixture was then cooled and filtered. The filtrate solution was concentrated by distillation at reduced pressure. The residue was dissolved with methanol (170 ml) and cooled down to 0~5° C. The titled compound 2 was obtained in crystalline form (50.3 g, yield 91%).

Step 2: Preparation of diethyl 2-[2-(2-amino-6-chloro-9H-purine-9-yl)-ethyl]-1,3-malonate (3)

To a dried 1 L reaction flask were added sequentially the DMF (380 g), anhydrous $K_2CO_3$ (55 g, 0.04 mol), intermediate compound 2 (98 g, 0.06 mol) and diethyl malonate (40 g, 0.0145 mol). The mixture was heated to 60° C. and stirred at 60° C. for 50 hours. Then the carbonate salt was removed by filtration. Solvent was then recovered by distillation at reduced pressure (keeping the temperature lower than 95° C. at all times). The residue was cooled to room temperature and dissolved with methanol (400 g). The title compound 3 was recovered after the methanol solution was kept at 0~4° C. for 4 hours (48 g, yield 95%).

Step 3: Preparation of 2-[2-(2-amino-6-chloro-9H-purine-9-yl)-ethyl]-1,3-propanediol (4)

To a 1 L flask was added the dichloromethane (350 ml) to dissolve the intermediate compound 3 (50 g, 0.013 mol), followed by $NaBH_4$ (17.5 g, 0.046 mol) and methanol (95 ml). The reaction mixture was stirred at 20~25° C. for 2 hours, then diluted with water (150 ml) and settled at room temperature. The separated organic layer was removed. The aqueous layer (along with the precipitated solid) was cooled down with an ice/water bath, and hydrochloric acid (25-30%) was added slowly till the solution became neutral. The product was obtained by cooling in an ice/water bath. The precipitate was collected by filtration, and then washed with cold brine. The collected diol 4 was dried under vacuum (30 g, yield 80%).

Step 4: Preparation of 2-[2-(2-amino-9H-purine-9-yl)-ethyl]-1,3-propanediol (5)

The diol 4 (25 g, 9.2 mmol) was dissolved with a mixed solvent of ethyl acetate (200 ml) and ethanol (100 ml) in a 1 L steel autoclave. The palladium charcoal (5 g) and triethylamine (12 g) were added as well. The reaction mixture was kept at 55° C. under hydrogen pressure (0.8 Mpa) for 4 hours. The reaction was regarded as completed when no hydrogen intake was observed. The catalyst was removed by filtration after cooling down. The filtrate was concentrated by distillation under reduced pressure. The residue was dissolved by addition of DCM and water. The separated aqueous layer was extracted with more DCM (30 ml×3). The combined organic solution was dried and distilled to remove solvent. The residue was dissolved with ethyl acetate (80 ml) and kept at room temperature for 4 hours. The product was collected by filtration and dried under vacuum (18 g, yield 82%).

Step 5: Preparation of Famciclovir

To a dry 1 L flask were added the intermediate diol 5 (50 g, 21.5 mmol), dichloromethane (500 ml), triethylamine (31 g, 30.6 mmol) and catalytic dimethylaminopyridine (3.1 g). The acetic anhydride (120 g, 31 mmol) was then added dropwise, keeping the solution at 25~30° C. The reaction mixture was stirred at room temperature for 10 hours. Water was added to dilute the reaction mixture, and 5% Sodium hydroxyl solution (5%) was added till the solution turned neutral. The separated organic layer was washed with water (200 ml×2), saturated brine and dried by sodium sulphate. The dichloromethane was then removed under reduced pressure, and residue was dissolved with boiling methanol (180 ml). The famciclovir crystallized out by keeping the methanol solution at 0~4° C. for 4 hours (60 g, yield 90%).

Hence a method for preparation of purine derivatives, such as famciclovir has been provided.

The invention claimed is:

1. A method for preparation of a purine derivative of formula I,

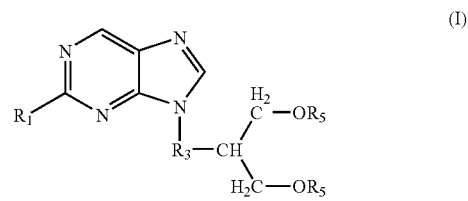

comprising (a) reacting a compound of formula VI

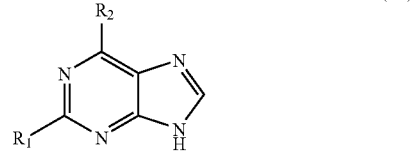

with X—$R_3$—X to form a compound of formula V

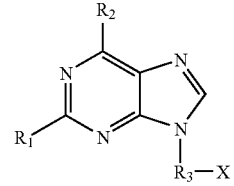

wherein $R_1$ is selected from the group consisting of amino, protected amino, hydroxyl, protected hydroxyl, $R_2$ is halo, $R_3$ is selected from the group consisting of $C_{1-6}$ alkyl and $C_{1-6}$ alkyl substituted by one or more substituents independently selected from the group consisting of amino, protected amino, hydroxyl, protected hydroxyl and $C_{1-6}$ alkyl, each $R_5$ is selected from the group consisting of $C_{1-6}$ alkyl carbonyl and $C_{1-6}$ alkyl carbonyl substituted by one or more substituents independently selected from the group consisting of halo, hydroxyl, protected hydroxyl and $C_{1-6}$ alkyl, and each X is independently a leaving group, subsequently (b) converting a compound of formula V to a compound of formula IV

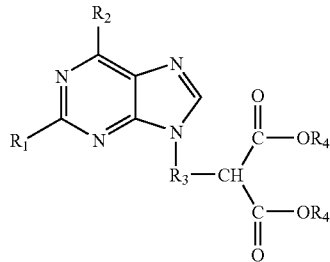
(IV)

by reacting the compound of formula V with CH$_2$(COOR$_4$)$_2$, wherein R$_4$ is selected from the group consisting of C$_{1-6}$ alkyl and C$_{1-6}$ alkyl substituted by one or more substituents independently selected from the group consisting of halo, amino, protected amino, hydroxyl, protected hydroxyl and C$_{1-6}$ alkyl, wherein the compound of formula V is converted to the compound of formula IV in a polar solvent in the presence of base, (c) reducing a compound of formula IV to yield a compound of formula III, (d) hydrogenating a diol of formula III

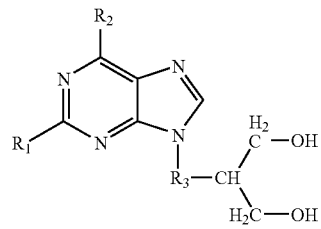
(III)

so as to yield a compound of formula II,

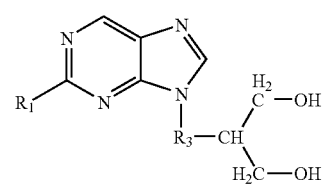
(II)

and (e) reacting the compound of formula II obtained in (d) with (R$_5$)$_2$O to form the compound of formula I.

2. The method of claim 1, wherein (a) is carried out in a polar solvent in the presence of base.

3. The method of claim 1, wherein (d) is carried out using hydrogen in the presence of a hydrogenation catalyst.

4. The method of claim 1, for preparation of famciclovir, wherein R$_1$ is amino, R$_2$ is chloro, R$_3$ is CH$_2$CH$_2$CH$_2$CH$_2$ and R$_5$ is acetyl.

5. A method for preparation of a purine derivative of formula I,

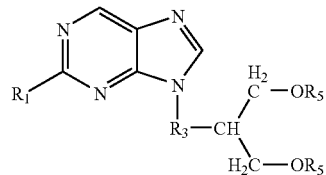
(I)

comprising (i) converting a compound of formula V

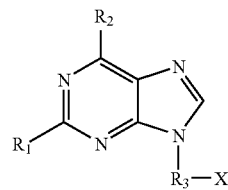
(V)

to a compound of formula IV

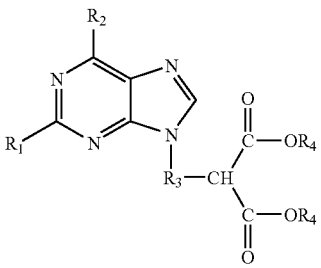
(IV)

wherein
R$_1$ is selected from the group consisting of amino, protected amino, hydroxyl, and protected hydroxyl, R$_2$ is halo, R$_3$ is selected from the group consisting of C$_{1-6}$ alkyl and C$_{1-6}$ alkyl substituted by one or more substituents independently selected from the group consisting of amino, protected amino, hydroxyl, protected hydroxyl and C$_{1-6}$ alkyl, and each R$_5$ is selected from the group consisting of C$_{1-6}$ alkyl carbonyl and C$_{1-6}$ alkyl carbonyl substituted by one or more substituents independently selected from the group consisting of halo, hydroxyl, protected hydroxyl and C$_{1-6}$ alkyl, and each X is independently a leaving group, by reacting the compound of formula V with CH$_2$(COOR$_4$)$_2$, wherein R$_4$ is selected from the group consisting of C$_{1-6}$ alkyl and C$_{1-6}$ alkyl substituted by one or more substituents independently selected from the group consisting of halo, amino, protected amino, hydroxyl, protected hydroxyl and C$_{1-6}$ alkyl, wherein the compound of formula V is converted to the compound of formula IV in a polar solvent in the presence of base, subsequently (ii) reducing a compound of formula IV to yield a compound of formula III.

(iii) hydrogenating a diol of formula III

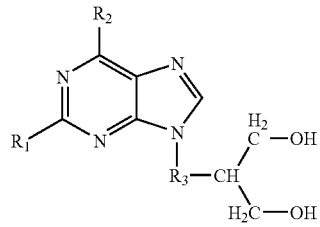
(III)

so as to yield a compound of formula of II

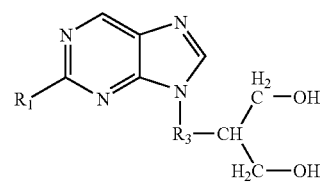
(II)

and (iv) reacting the compound of formula II obtained in (iii) with $(R_5)_2O$ to form the compound of formula I.

6. The method of claim 5, wherein the reaction of a compound of formula II with $(R_5)_2O$ is carried out in an inert organic solvent.

7. The method of 6, wherein the reaction of a compound of formula II with $(R_5)_2$ is carried out in the presence of an amine.

8. The method of claim 7, wherein the amine is a tertiary amine.

9. The method of claim 5, for preparation of famciclovir, wherein $R_1$ is amino, $R_2$ is chloro, $R_3$ is $CH_2CH_2CH_2CH_2$ and $R_5$ is acetyl.

10. A method for preparation of a purine derivative of formula I,

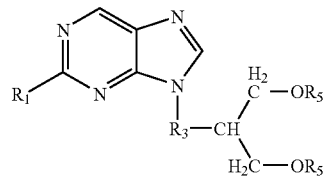
(II)

comprising:
(a) reducing a compound of formula IV

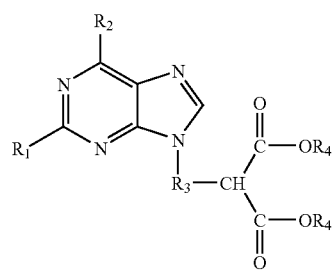
(IV)

to form a compound of formula III

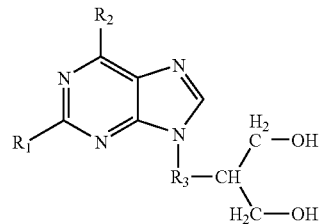
(III)

wherein
$R_1$ is selected from the group consisting of amino, protected amino, hydroxyl, and protected hydroxyl,
$R_2$ is halo,
$R_3$ is selected from the group consisting of $C_{1-6}$ alkyl and $C_{1-6}$ alkyl substituted by one or more substituents independently selected from the group consisting of amino, protected amino, hydroxyl, protected hydroxyl and $C_{1-6}$ alkyl,
each $R_4$ is selected from the group consisting of $C_{1-6}$ alkyl and $C_{1-6}$ alkyl substituted by one or more substituents independently selected from the group consisting of halo, amino, protected amino, hydroxyl, protected hydroxyl and $C_{1-6}$ alkyl, and
each $R_5$ is selected from the group consisting of $C_{1-6}$ alkyl carbonyl and $C_{1-6}$ alkyl carbonyl substituted by one or more substituents independently selected from the group consisting of halo, hydroxyl, protected hydroxyl and $C_{1-6}$ alkyl, subsequently (b) hydrogenating the diol of formula III so as to yield a compound of formula of II, and

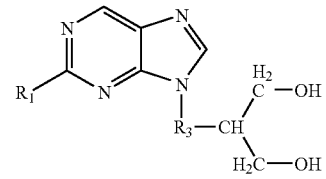
(II)

(c) reacting the compound of formula II obtained in (b) with $(R_5)_2O$ to form the compound of formula I.

11. A method for preparation of a purine derivative of formula I, comprising:

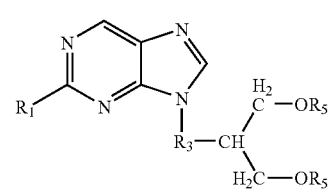
(I)

(a) hydrogenating a diol of formula III

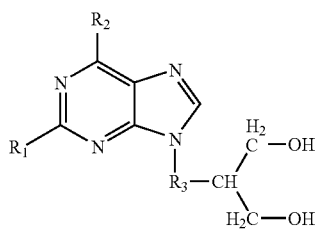
(III)

so as to yield a compound of formula of II

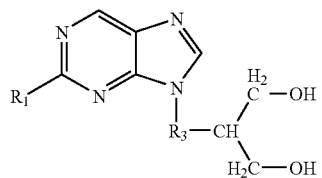
(I)

wherein

R$_1$ is selected from the group consisting of amino, protected amino, hydroxyl, and protected hydroxyl, R$_2$ is halo, R$_3$ is selected from the group consisting of C$_{1-6}$ alkyl and C$_{1-6}$ alkyl substituted by one or more substituents independently selected from the group consisting of amino, protected amino, hydroxyl, protected hydroxyl and C$_{1-6}$ alkyl, and each R$_5$ is selected from the group consisting of C$_{1-6}$ alkyl carbonyl and C$_{1-6}$ alkyl carbonyl substituted by one or more substituents independently selected from the group consisting of halo, hydroxyl, protected hydroxyl and C$_{1-6}$ alkyl, and (b) reacting the compound of formula II obtained in (a) with (R$_5$)$_2$O to form the compound of formula I.

\* \* \* \* \*

UNITED STATES PATENT AND TRADEMARK OFFICE
CERTIFICATE OF CORRECTION

PATENT NO. : 7,601,835 B2
APPLICATION NO. : 11/270777
DATED : October 13, 2009
INVENTOR(S) : Liang He et al.

Page 1 of 1

It is certified that error appears in the above-identified patent and that said Letters Patent is hereby corrected as shown below:

On the Title page, Item (73) Assignee:

should read -- Chongqing Shenghuaxi Pharmaceutical Co., LTD, Chongqing, CH; Arrow International Limited Valetta, MT --.

Signed and Sealed this
Eighth Day of March, 2011

David J. Kappos
*Director of the United States Patent and Trademark Office*